United States Patent

Nakane et al.

[11] Patent Number: 4,652,578
[45] Date of Patent: Mar. 24, 1987

[54] 7-OXABICYCLOHEPTANE SUBSTITUTED AMIDE PROSTAGLANDIN ANALOGS

[75] Inventors: Masami Nakane, Hopewell; Steven E. Hall, Ewing Township, Mercer County, both of N.J.

[73] Assignee: E. R. Squibb & Sons, Inc., Princeton, N.J.

[21] Appl. No.: 832,543

[22] Filed: Feb. 24, 1986

[51] Int. Cl.⁴ ............... C07D 493/08; C07D 405/14; A61K 31/34; A61K 31/41
[52] U.S. Cl. .................... 514/382; 514/469; 548/252; 549/463
[58] Field of Search ............ 549/463; 548/252; 514/382, 469

[56] References Cited

U.S. PATENT DOCUMENTS

| | | | |
|---|---|---|---|
| 4,416,896 | 11/1983 | Nakane et al. | 424/285 |
| 4,418,076 | 11/1983 | Nakane et al. | 424/285 |
| 4,456,617 | 6/1984 | Nakane et al. | 424/285 |
| 4,526,901 | 7/1985 | Nakane | 514/469 |

FOREIGN PATENT DOCUMENTS

| | | |
|---|---|---|
| 0043292 | 8/1982 | European Pat. Off. |
| 0082646 | 6/1983 | European Pat. Off. |
| 2039909 | 8/1980 | United Kingdom |

Primary Examiner—Robert Gerstl
Attorney, Agent, or Firm—Lawrence S. Levinson; Burton Rodney

[57] ABSTRACT

Cis-exo 7-oxabicycloheptane substituted amide prostaglandin analogs are provided having the structural formula

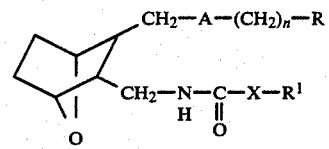

wherein A is $-CH=CH-$ or $-CH_2-CH_2-$; n is 1 to 5; R is $CO_2H$, $CO_2$alkyl, $CO_2$alkali metal, $CO_2$polyhydroxyamine salt, $-CH_2OH$,

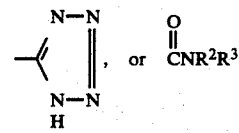

wherein $R^2$ and $R^3$ are the same or different and are H, lower alkyl, hydroxy, lower alkoxy or aryl, at least one of $R^2$ and $R^3$ being other than hydroxy and lower alkoxy; X is O, NH, $CH=CH$, or $-(CH_2)_x$ wherein x is 0 or 1; and $R^1$ is lower alkyl, lower alkenyl, lower alkynyl, aryl, arylalkyl, lower alkoxy, aryloxy, amino, alkylamino, arylamino, arylthio or alkylthio.

The compounds are cardiovascular agents useful, for example, in the treatment of thrombotic disease.

17 Claims, No Drawings

7-OXABICYCLOHEPTANE SUBSTITUTED AMIDE PROSTAGLANDIN ANALOGS

DESCRIPTION OF THE INVENTION

The present invention relates to cis-exo isomers of 7-oxabicycloheptane substituted amide prostaglandin analogs which are cardiovascular agents useful, for example, in the treatment of thrombotic disease. These compounds have the structural formula

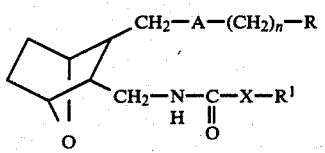

which include only the cis-exo stereoisomers thereof, wherein A is —CH=CH— or —CH$_2$—CH$_2$—; n is 1 to 5; R is CO$_2$H, CO$_2$ alkyl, CO$_2$ alkali metal, CO$_2$ polyhydroxyamine salt, —CH$_2$OH,

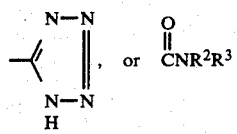

wherein R$^2$ and R$^3$ are the same or different and are H, lower alkyl, hydroxy, lower alkoxy or aryl at least one of R$^2$ and R$^3$ being other than hydroxy and lower alkoxy; X is —(CH$_2$)$_x$— (wherein x is 0 or 1), —CH=CH—, —O— or —NH—; and R$^1$ is lower alkyl, lower alkenyl, lower alkynyl, aryl, arylalkyl, lower alkoxy, aryloxy, amino, alkylamino, arylamino, arylthio or alkylthio.

Thus, the cis-exo isomers of the present invention include the following types of compounds:

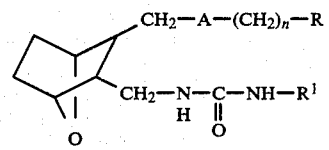

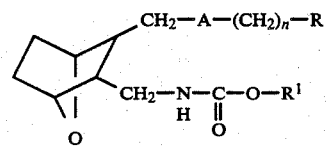

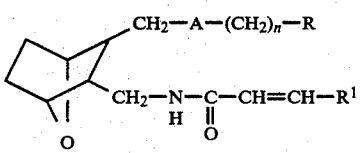

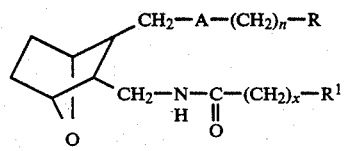

The term "lower alkyl" or "alkyl" as employed herein alone or as part of another group includes both straight and branched chain hydrocarbon radicals of from 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such group including a halo-substituent, such as F, Br, Cl or I or CF$_3$, an alkoxy substituent, an aryl substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent, or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups 1 or 2 lower alkoxy groups. 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The terms "lower alkoxy", "alkoxy", aryloxy or "aralkoxy" and lower "alkylthio", alkylthio, arylthio or aralkylthio as employed herein alone or as part of another group includes any of the above lower alkyl, alkyl or aralkyl groups linked to an oxygen atom or sulfur atom as the case may be.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, and which may include 1 or 2 aryl and/or aralkyl substituents, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3- nonynyl, 4-decynyl, 3-undecynyl, 4-dodecynyl and the like.

The term $(CH_2)_n$ includes straight or branched chain radicals having from 1 to 5 carbons in the normal chain and may contain one or more lower alkyl and/or halogen substituents. Examples of $(CH_2)_n$ groups include

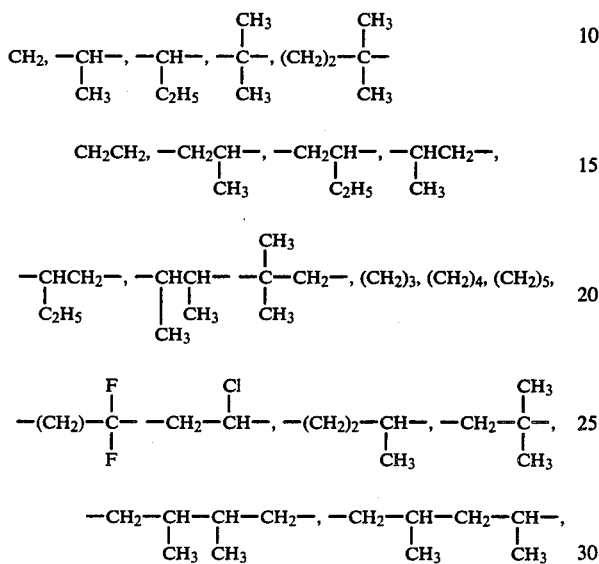

and the like.

The term "polyhydroxyamine salt" refers to glucamine salt or tris(hydroxymethyl)aminomethane.

The term "halogen" or "halo" as used herein refers to chlorine, bromine, fluorine, iodine and $CF_3$, with chlorine or fluorine being preferred.

Preferred are those cis-exo isomers of formula I wherein A is a —CH═CH—, n is 2 to 4, X is —CH$_2$—, —O— or —NH—; R is $CO_2H$; and $R^1$ is lower alkyl, such as pentyl, hexyl, lower alkenyl, such as 1-pentenyl; aryl, such as phenyl; or aralkyl.

The cis-exo isomers of formula I of the invention may be prepared as described below.

A. Preparation of phthalimide starting materials

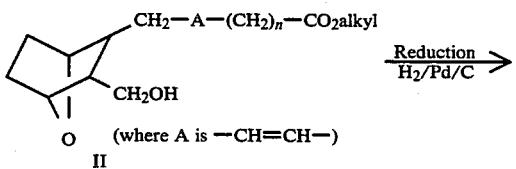

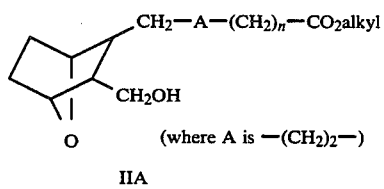

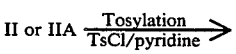

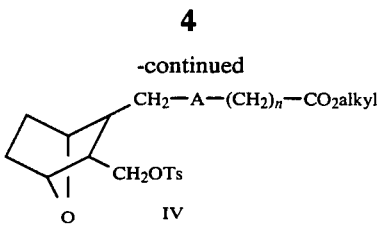

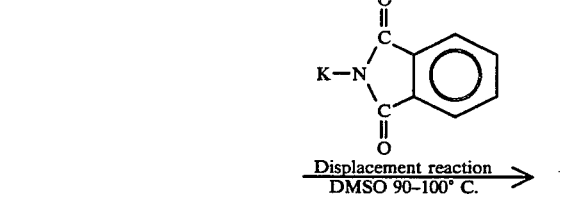

B. Where X is —NH—

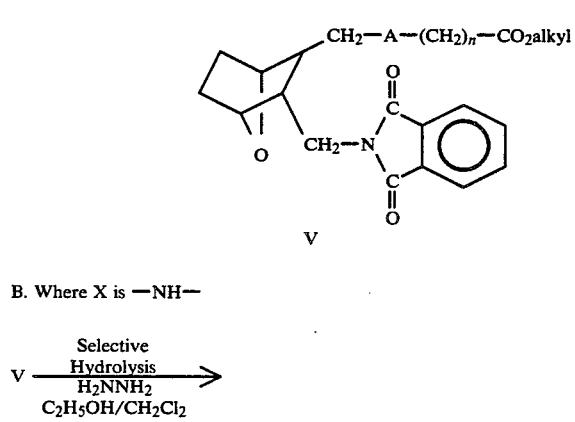

C. Where X is —O—

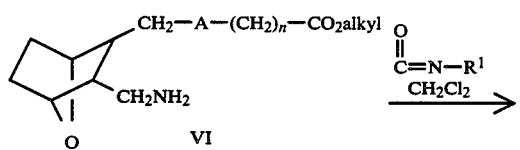

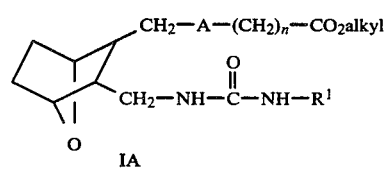

D. Where X is —$(CH_2)_x$— where x is 0 or 1

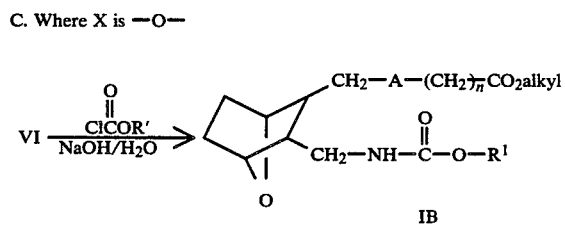

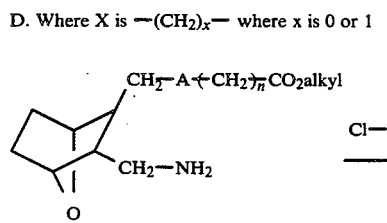

-continued

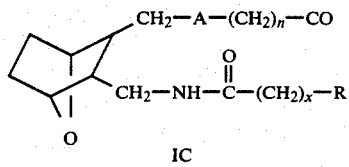
IC

D'. Where X is —CH=CH—

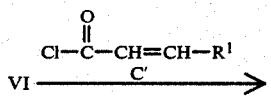

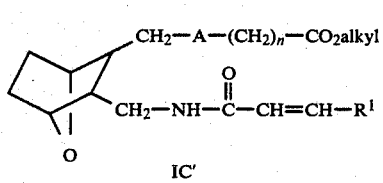
IC'

E. Where R is $\overset{O}{\overset{\|}{C}}NR^2R^3$
(wherein $R^2$ and $R^3$ are other than hydroxy or alkoxy)

IA, IB, IC, IC' $\xrightarrow{HNR^2R^3}$

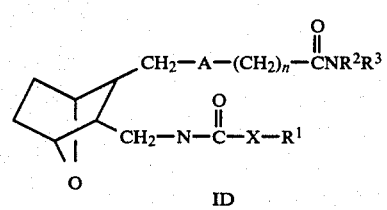
ID

F. Where R is 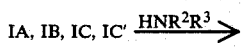 and A is CH=CH

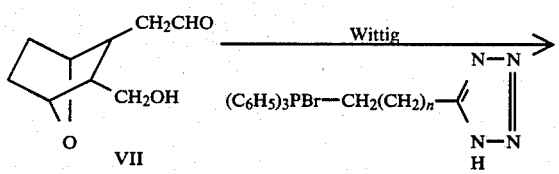

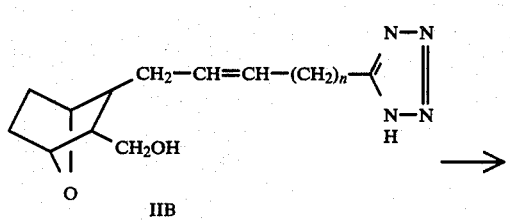
IIB

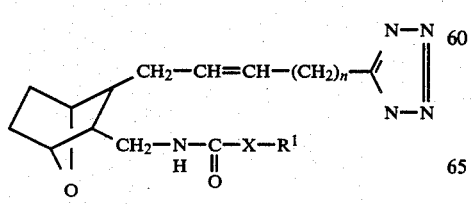
IE

F'. Where R is 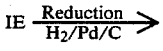 and A is $(CH_2)_2$

IE $\xrightarrow[H_2/Pd/C]{\text{Reduction}}$

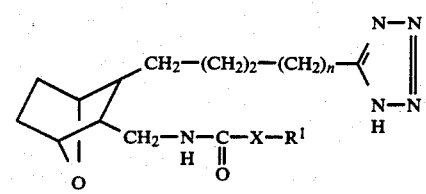
IF

G. Where R is $CH_2OH$

IB, IC, IC', or ID $\xrightarrow[LiNH_4]{NaBH_4 \text{ or}}$

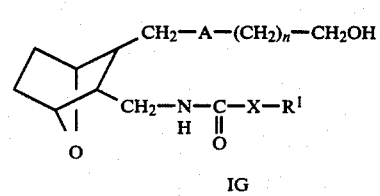
IG

H. Where R is $CO_2H$

IA, IB, IC, IC', or ID $\xrightarrow{\text{Hydrolysis} \atop LiOH, HCl}$

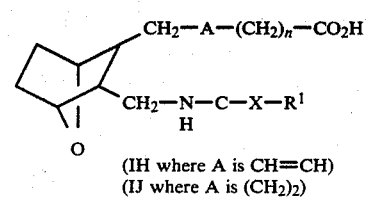

(IH where A is CH=CH)
(IJ where A is $(CH_2)_2$)

J. Where R is $\overset{O}{\overset{\|}{C}}\overset{\,}{\underset{R^2}{N}}-OR^{3'}$ IH or IJ $\xrightarrow[\text{(2) } HN\overset{OR^{3'}}{\underset{R^2}{\,}} \cdot HCl/(C_2H_5)_3N]{\text{Hydroxamate Formation} \atop \text{(1) ClCOCOCl, benzene, } N_2, R.T. \atop cat. \text{ DMF}}$ (where $R^{3'}$ is H or alkyl)

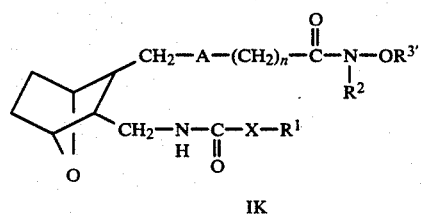
IK

As seen in reaction sequence "A", starting phthalimides V for use in preparing compounds of the invention

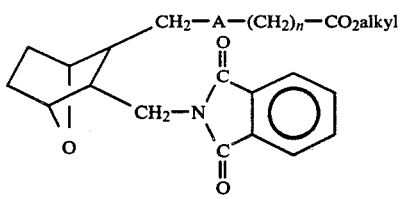 V are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V.

As seen in reaction sequence "B", compounds of the invention wherein X is —NH— and R is $CO_2$-alkyl, may be prepared by subjecting the phthalimide V to selective hydrolysis by dissolving V in methylene chloride and ethanol under an inert atmosphere such as argon and reacting with anhydrous hydrazine to form the amine VI

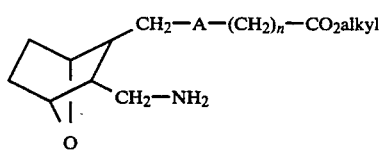 VI

The amine VI is reacted with isocyanate of the structure A

 A in methylene chloride to form ester compound IA

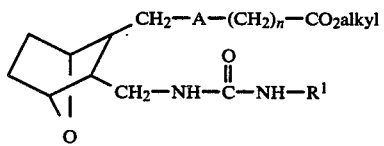 IA

Compounds of formula IB wherein X is —O— and R is $CO_2$ alkyl may be prepared as described in reaction sequence "C" wherein amine VI is treated with chloroformate B

 B in the presence of aqueous base such as NaOH to form ester IB

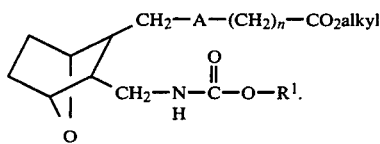 IB

In the reaction sequence identified as "D" and "D'", compounds of the invention wherein X is —$(CH_2)_x$— and —CH=CH—, respectively, and R is $CO_2$ alkyl, that is,

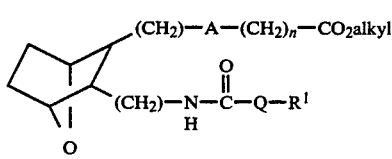

IC where Q is —$(CH_2)_x$—
IC' where Q is —CH=CH— are prepared by treating the amine VI with acid chloride

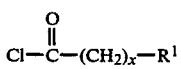 C or

 C' in the presence of base such as NaOH, $NaCO_3$ or $NaHCO_3$ to form acid chloride IC or IC'.

In reaction sequence "E", amides of the invention of structure ID

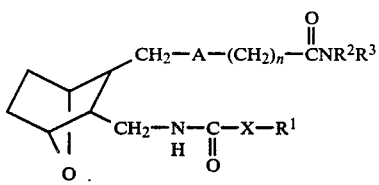 ID wherein $R^2$ and $R^3$ are independently H, alkyl or aryl are prepared by treating ester IA to IC with an amine of the structure $HNR^2R^3$. E Compounds of the invention wherein R is tetrazole 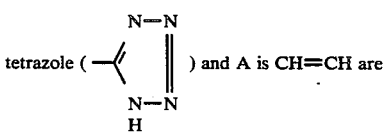 ) and A is CH=CH are prepared as described in reaction sequence "F" wherein alcohol VII

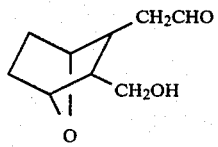

(prepared as described in U.S. Pat. No. 4,143,054) is reacted with a Wittig reagent of the structure F

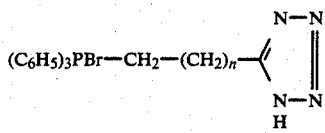

in the presence of a base, such as potassium t-butoxide or sodium hydride-dimethyl sulfoxide to form the hydroxymethyl compound IIB

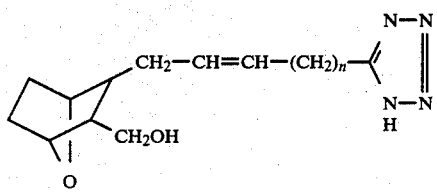

which may then be employed in reaction sequences "A" to "D" in place of compounds II or IIA to form compounds of the invention IE where A is —CH=CH— or IF where A is (CH$_2$)$_2$.

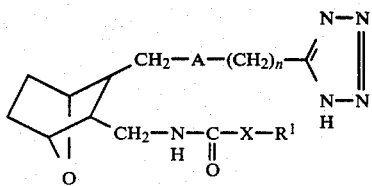

Alternatively, as seen in reaction sequence F', compound IF may be prepared by reducing compound IE by treating with H$_2$ in the presence of palladium on charcoal.

As seen in reaction sequence "G", compounds of the invention wherein R is CH$_2$OH may be prepared by reducing esters IB to ID by treatment with sodium borohydride or lithium borohydride to form compounds of the invention IG

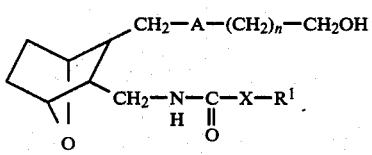

Referring to reaction sequence "H", the esters IB to ID can be converted to the free acid, that is, to

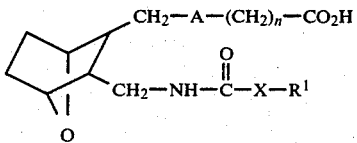

IH (A is —CH=CH—)
IJ (A is (CH$_2$)$_2$)

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IH and IJ.

In the reaction sequence identified as "J" where in Formula I, R is

wherein R$^{3'}$ is H or alkyl, a solution of acid dissolved in an inert organic solvent such as THF is treated with carbonyldiimidazole and the mixture is stirred at room temperature under nitrogen. The resulting activated acid is treated with amine hydrochloride H

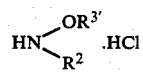

(wherein R$^{3'}$ is H or alkyl, employing a molar ratio of acid chloride:H of within the range of from about 0.3:1 to about 1:1 and preferably from about 0.5:1) and triethylamine in tetrahydrofuran to form the hydroxamate IK.

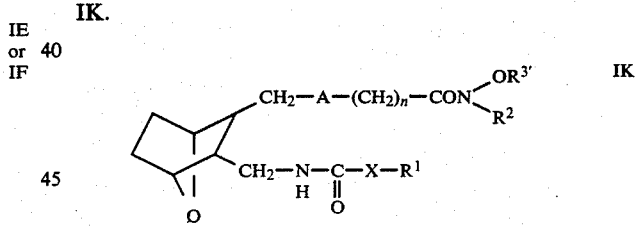

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

The compounds of the invention are of the cis-exo form and may be prepared as shown in the working Examples which follow and by employing starting materials following the procedures as outlined in U.S. Pat. No. 4,143,054 and described above. Examples of such stereoisomers are set out below.

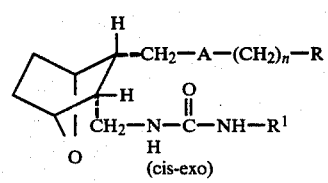

-continued

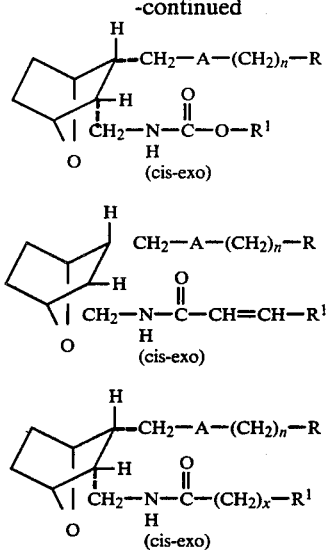

The nucleus in each of the compounds of the invention is depicted as

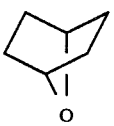

for matter of convenience; it will also be appreciated that the nucleus in the compounds of the invention may be depicted as

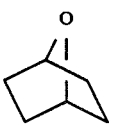

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionaly serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1β,2α(5Z),3α,4β]-7-[3-[[[(Phenylmethoxy)carbonyl-]amino]methyl]-7-oxabicyclo[2.2.1]hept-2-yl]-5-heptenoic acid, methyl ester

A.

[1β,2α(5Z),3α,4β]-7-[3-(Tosyloxymethyl)-7-oxabicyclo[2.2.1]hept-2-yl]-5-heptenoic acid, methyl ester Tosyl chloride (4.256 g, 22.4 mmol) dissolved in $CH_2Cl_2$ (30 ml) was added dropwise to a magnetically stirred solution of [1β,2α(5Z),3α,4β]-7-[3-(hydroxymethyl)-7-oxabicyclo[2.2.1]hept-2-yl]-5-heptenoic acid, methyl ester (prepared as described in U.S. Pat. No. 4,143,054 (3 g, 11.2 mmol) in pyridine (30 ml) at 0° C. After completion of the addition, the reaction was warmed to room temperature and stirred overnight. The reaction was poured into ice/$H_2O$ and stirred for 30 minutes. The products were extracted with EtOAc (80 ml×3). The combined EtOAc layers were washed with 3N-HCl (40 ml×3), saturated $NaHCO_3$, brine and dried over $MgSO_4$. Filtration and evaporation of solvent gave a white solid, which was crystallized from isopropyl ether to give the corresponding title tosylate in the form of needle crystals (4.23 g, 89%), m.p. 68°-70° C.

B.

[1β,2α(5Z),3α,4β]-7-[(3-(Aminomethyl)-7-oxabicyclo[2.2.1]hept-2-yl]-5-heptenoic acid, methyl ester The title A tosylate was subjected to a Gabriel synthesis to form the corresponding amino compound as described below.

The potassium phthalimide used was purified prior to use by boiling 5 g thereof with 9 ml acetone for 15 minutes, filtering while hot and washing with 5 ml acetone. The remaining solid was dried in vacuo for 6 hours at 100° C. prior to use.

The title A tosylate (8.11 g, 19.2 mmol) and purified potassium phthalimide (6.4 g, 34.6 mmol, 1.8 equiv.) in dimethylsulfoxide (70 ml, Burdick & Jackson) were heated at 90°-100° C. for 2½ hours (checked by TLC $Et_2O$-pet ether 2:1, no tosylate remaining). After cooling to room temperature, water (90 ml) was added. Material began precipitating. The mixture was poured into ice water (~350 ml) and stirred 30 minutes. The straw colored solid was harvested by filtration and washed with more water. The solid was dissolved in warm ethyl acetate (150 ml), washed with water (3{50 ml), dried ($MgSO_4$), filtered and freed of solvent in vacuo. The remaining solid (7.88 g) was recrystallized from isopropyl ether (~150 ml) to give corresponding phthalimide (6.35 g, 83%) TLC. $Et_2O$-hexane 2:1, UV+vanillin $R_f$=0.38, trace 0.09.

The above phthalimide (5.05 g, 13.8 mmol) was dissolved in distilled $CH_2Cl_2$ (24 ml) and distilled ethanol (104 ml) in an argon atmosphere. Anhydrous hydrazine (0.78 ml, 25.6 mmol) was added. The mixture was stirred at room temperature. After 8 hours an additional 0.2 ml of hydrazine was added and the mixture was stirred an additional 15 hours at room temperature. A white solid was removed by filtration and washed with more $CH_2Cl_2$. The filtrate was taken to dryness in vacuo (on the pump at end). Cold 0.5N HCl solution (80 ml) was added. A small amount of white solid was removed by filtration and washed with additional 0.5N HCl solution (80 ml). The acidic solution was washed with ether (2×100 ml) and then basified with solid $K_2CO_3$. The amine was extracted into $CHCl_3$ (3×100 ml), dried ($MgSO_4$) and freed of solvent in vacuo leaving a yellow oil. Ether (100 ml) was added to this oil. Some solid was insoluble. After cooling in an ice bath, the solid was removed by filtration. The solvent was removed from the filtrate in vacuo leaving title amine as a pale yellow oil (2.441 g, 71%). NMR spectra and TLC indicated some minor impurities. The material was used without further purification.

C. [1β,2α(5Z),3α,4β]-7-[3-[[[(Phenylmethoxy)carbonyl]amino]methyl]-7-oxabicyclo[2.2.1]hept-2-yl]-5-heptenoic acid, methyl ester Part B amine (248.5 mg, 0.93 mmol) was suspended in water (1 ml) and cooled in an ice bath. Benzylchloroformate (0.156 ml), 1.1 mmol) and 1N NaOH (to maintain pH at 7-9) were added simultaneously. The ice bath was removed and the mixture was stirred at room temperature 30 minutes (adding NaOH solution as necessary). The product was extracted into ethyl acetate (2×50 ml), washed with saturated NaCl solution (2×20ml), dried ($MgSO_4$) and freed of solvent in vacuo leaving a colorless oil (295 mg). This was chromatographed on silica gel 60 (30 g), eluting with ether-pet ether (2:3 and 3:2) to give title ester (228 mg, 61%) as an oil. TLC: silica gel, $Et_2O$-pet ether 3:2, vanillin $R_f$=0.24.

EXAMPLE 2

[1β,2α(5Z),3α,4β]-7-[3-[[[(Phenylmethoxy)carbonyl]amino]methyl]-7-oxabicyclo[2.2.1]hept-2-yl]-5-heptenoic acid The Example 1 methyl ester (210 mg, 0.523 mmol) was dissolved in distilled THF (20 ml) and water (5 ml) in an argon atmosphere. Lithium hydroxide solution (5.2 ml of 1N) was added and the mixture was stirred at room temperature 3.5 hours. The mixture was neutralized by adding 1N HCl solution (5.2 ml) and solid NaCl was added to separate the layers. The aqueous layer was extracted with $CHCl_3$ (3×20 ml). The combined organic layers (THF and $CHCl_3$) were washed with saturated NaCl solution (2×20 ml), dried ($MgSO_4$) and freed of solvent in vacuo leaving an oil (195 mg). This was chromatographed on silica gel 60 (20 g) eluting with 2% MeOH in $CH_2Cl_2$ to give 172 mg (85%) of title acid. The oil became a waxy solid on standing in the freezer. TLC: silica gel, 5% MeOH in $CH_2Cl_2$, UV and vanillin; $R_f$=0.42.

Anal Calcd for $C_{22}H_{29}O_5N$: C, 68.19; H, 7.54; N, 3.62. Found: C, 67.84; H, 7.60; N, 3.61.

EXAMPLE 3

[1α,2β(5Z),3β,4α]-7-[3-[[(1-Oxo-3-phenylpropyl)amino]methyl]-7-oxabicyclo[2.2.1]hept-2-yl]-5-heptenoic acid, methyl ester Example 1 Part B amine (210 mg) was suspended in $H_2O$ (1 ml). The pH was adjusted to 9 with 1N-NaOH under vigorous stirring. 3-Phenylpropionic acid chloride (135 mg) was added dropwise, maintaining the pH between 7 and 10. The reaction was stirred an additional 30 minutes after completion of the addition, at room temperature. The products were extracted with EtOAc (50 ml×2), which was washed with brine and dried over $MgSO_4$. Filtration and evaporation of solvent gave a yellow oil (256 mg), which was purified by a silica gel column (silica 60, 10 g) eluted with ether to give a white solid (102.7 mg, 0.257 mmole, 37%).

EXAMPLE 4

[1α,2β(5Z),3β,4α]-7-[3-[[(1-Oxo-3-phenylpropyl)amino]methyl]-7-oxabicyclo[2.2.1]hept-2-yl]-5-heptenoic acid Example 3 ester (102.7 mg) was dissolved in THF (13 ml) and $H_2O$ (2.6 ml). 1N-LiOH (2.6 ml) was added and the reaction was stirred for 7 hours at room temperature. 1N-HCl (2.6 ml) was added and the products were extracted with EtOAc (50 ml×3), which was washed with brine (50 ml) and dried over $MgSO_4$. Filtration and evaporation of solvent gave a yellow oil, which was purified by silica gel column (silica CC-7, 10 g) eluted with 3% MeOH in $CH_2Cl_2$ to give title acid (88 gm, 0.23 mmole, 89%).

Anal Calcd for $C_{23}H_{31}O_4N.0.2H_2O$: C, 70.91; H, 8.22; N, 3.61. Found: C, 70.96; H, 8.24; N, 3.40.

EXAMPLE 5

[1β,2α(5Z),3α,4β]-7-[3-[[[[(Phenylmethyl)amino]carbonyl]amino]methyl]-7-oxabicyclo[2.2.1]hept-2-yl]-5-heptenoic acid, methyl ester Example 1, Part B amine (248 mg, 0.93 mmol) was dissolved in distilled $CH_2Cl_2$ (20 ml) in an argon atmosphere. After cooling in an ice bath, benzyl isocyanate (0.136 ml, 1.1 mmol) was added. The mixture was stirred at 0°-5° C. for 45 minutes and at room temperature 4 hours. The solvent was removed in vacuo and the remaining oil was chromatographed on silica gel 60 (20 g). The product was eluted with 1.5% MeOH in $CH_2Cl_2$ to give 275 mg (74%) of title compound. TLC: silica gel, 5% MeOH in $CH_2Cl_2$, UV and vanillin $R_f$=0.42.

EXAMPLE 6

[1α,2β(5Z),3β,4α]-7-]3-[[[[(Phenylmethyl)amino]carbonyl]amino]methyl]-7-oxabicyclo[2.2.1]hept-2-yl]-5-heptenoic acid The Example 5 methyl ester (260 mg, 0.65 mmol) was dissolved in distilled tetrahydrofuran (20 ml) and water (5 ml) in an argon atmosphere. 1N Lithium hydroxide solution (6.5 ml) was added and the mixture was stirred at room temperature for 6 hours and then neutralized by adding 1N HCl solution (6.5 ml). Solid NaCl was added to separate the layers. The aqueous layer was extracted with $CHCl_3$ (3×20 ml). The combined organic layers (THF and $CHCl_3$) were washed with saturated NaCl solution (2×20 ml), dried ($MgSO_4$), and freed of solvent in vacuo leaving a colorless oil. This was chromatographed on silica gel 60 (20 g) eluting with 5% MeOH in CH$_2$Cl$_2$ to give title acid as an oil, 214 mg (85%). TLC: silica gel, 8% MeOH in CH$_2$Cl$_2$, UV and vanillin R$_f$=0.47.

Anal Calcd for C$_{22}$H$_{30}$O$_4$N$_2$.0.25H$_2$O: C, 67.58; H, 7.86; N, 7.16. Found: C, 67.62; H, 7.86; N, 7.11.

EXAMPLE 7

(1β,2α,3α,4β)-7-[3-[[[(Phenylmethoxy)carbonyl]amino]methyl]-7-oxabicyclo[2.2.1]hept-2-yl]heptanoic acid, methyl ester

A.

(1β,2α,3α,4β)-7-[3-(Hydroxymethyl)-7-oxabicyclo[2.2.1]hept-2-yl]heptanoic acid, methyl ester To 800 mg (3.0 mmole) of the [1β,2α(Z),3α,4β]-7-[3-(hydroxymethyl)-7-oxabicyclo[2.2.1]-hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

(1β,2α,3α,4β)-7-[3-[[[(Phenylmethoxy)carbonyl]amino]methyl]-7-oxabicyclo[2.2.1]hept-2-yl]heptanoic acid, methyl ester Following the procedure of Example 1 except substituting the Part A alcohol-ester for the alcohol ester employed in Example 1 Part A, the title product is obtained.

EXAMPLE 8

[1α,2β(Z),3β,4α]-6-[3-[[(1-Oxo-3-phenylpropyl)amino]methyl]-7-oxabicyclo[2.2.1]hept-2-yl]-1-(1H-tetrazol-5-yl)-4-hexene

A.

[1α,2β(Z),3β,4α]-6-[3-Hydroxymethyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S. Pat. No. 4,143,054) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO$_3$ solution, washed with 100 ml of ether, acidified with dilute HCl to pH 3, and extracted with three 500 ml portions of ethyl acetate. The combined organic solutions are dried over anhydrous MgSO$_4$, and purified by silica chromatography using a 5% methanol in methylene chloride eluant to provide 2 g of title A compound.

B.

[1α,2β(5Z),3β,4α]-6-[3-[[(1-Oxo-3-phenylpropyl)amino]methyl]-7-oxabicyclo[2.2.1]hept-2-yl]-1-(1H-tetrazol-5yl)-4-hexene Following the procedure of Examples 3 and 4 except substituting the Part A compound for the hydroxymethyl compound used in preparing the Example 3 Part A compound, the title compound is obtained.

EXAMPLE 9

[1β,2α(5Z),3α,4β]-7-[3-[[[(Phenylmethyl)amino]carbonyl]amino]methyl]-7-oxabicyclo[2.2.1]hept-2-yl]-N-hydroxy-N-methyl-5-heptenamide A solution of Example 6 acid (0.82 mmole) in dry THF (5.0 ml) is treated with carbonyldiimidazole (0.90 mmole or 1.1 eq.) and stirred at 0° C. for 1 hour and at room temperature for 1 hour. Methylhydroxylamine hydrochloride (139.8 mg; 1.64 mmole; 2 eq.) and triethylamine (0.34 ml; 2.46 mmole; 3 eq.) are added to the reaction. The mixture is stirred at 0° under nitrogen for 30 minutes and at room temperature for 5.5 hours, diluted with water (10 ml) and extracted twice with dichloromethane (50 ml). The organic extract is washed with 1N HCl (10 ml), 5% NaHCO$_3$ (5 ml) and water (10 ml), dried (anhydrous MgSO$_4$), filtered and evaporated to dryness giving the crude product, which is purified by silica gel column to afford the title compound.

EXAMPLE 10

[1β,2α(5Z),3α,4β]-7-[3-[[[(Phenylmethoxy)carbonyl]amino]methyl]-7-oxabicyclo[2.2.1]hept-2-yl]-5-heptene-1-ol LiBH$_4$ (84 mg) is added to a magnetically stirred solution of ester prepared in Example 1 (310 mg) at 0° C. After hydrogen evolution was subsided, the reaction is allowed to warm to room temperature and stirred overnight (16 hours). Saturated NH$_4$Cl (10 ml) is added and stirred for 1 hour. Most of the MeOH is removed in vacuo and the residue is partitioned between EtOAc (50 ml) and brine (10 ml). The water layer is reextracted with EtOAc (40 ml×2). The combined organic layers are washed with brine (30 ml) and dried over MgSO$_4$. Filtration and evaportion of solvent give a crude product, which is purified by silica gel column. The title compound is thus obtained.

EXAMPLES 11 TO 38

Following the procedures outlined in the specification and described in the above working Examples, the following compounds may be prepared.

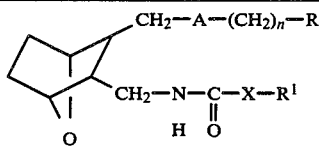

| Ex. No. | A | (CH$_2$)$_n$ | R | X | R$^1$ |
|---|---|---|---|---|---|
| 11. | CH=CH | CH$_2$ | CO$_2$H | O | —C$_5$H$_{11}$ |
| 12. | (CH$_2$)$_2$ | (CH$_2$)$_2$ | CH$_2$OH | NH | —CH$_3$ |

-continued

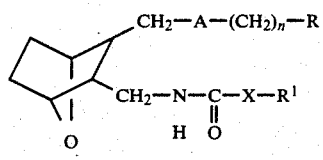

| Ex. No. | A | (CH$_2$)$_n$ | R | X | R$^1$ |
|---|---|---|---|---|---|
| 13. | CH=CH | (CH$_2$)$_3$ | tetrazole (N=N, N-N-H) | CH$_2$ | —CH=CH—CH$_3$ |
| 14. | (CH$_2$)$_2$ | (CH$_2$)$_4$ | $\underset{CN(CH_3)C_2H_5}{\overset{O}{\|}}$ | — | —CH=CHCH$_3$ |
| 15. | CH=CH | (CH$_2$)$_5$ | $\underset{\underset{CH_3}{\|}}{\overset{O}{\underset{CN-OH}{\|}}}$ | —CH=CH— | C$_6$H$_5$ |
| 16. | CH=CH | —CH(CH$_3$)— | $\overset{O}{\underset{CN-OCH_3,H}{\|}}$ | CH$_2$ | —CH$_2$—C≡C—CH$_3$— |
| 17. | (CH$_2$)$_2$ | —C(CH$_3$)$_2$— | $\underset{\underset{CH_3}{\|}}{\overset{O}{\underset{CN-OC_2H_5}{\|}}}$ | NH | —CH$_2$SC$_6$H$_5$ |
| 18. | (CH$_2$)$_2$ | (CH$_2$)$_4$ | $\overset{O}{\underset{CNHC_6H_5}{\|}}$ | O | C$_6$H$_5$ |
| 19. | CH=CH | —C(CH$_3$)$_2$—CH$_2$— | CO$_2$Li | O | CH$_2$C$_6$H$_5$ |
| 20. | CH=CH | —CH(CH$_3$)—CH(CH$_3$)— | CO$_2$Na | NH | —(CH$_2$)$_2$C$_6$H$_5$ |
| 21. | (CH$_2$)$_2$ | —C(CH$_3$)(F)—CH$_2$— | CO$_2$glucamine salt | —CH$_2$— | —C$_6$H$_4$—p-CH$_3$ |
| 22. | CH=CH | —CF—CF— | CO$_2$tris salt | — | —C$_6$H$_4$—p-OH |
| 23. | (CH$_2$)$_2$ | —C(F)$_2$—CH$_2$— | CH$_2$OH | O | —CH$_2$CH$_3$ |
| 24. | (CH$_2$)$_2$ | —(CH$_2$)$_5$— | tetrazole (N=N, N-N-H) | —CH=CH— | —CH$_2$CH$_3$ |
| 25. | CH=CH | —CH$_2$—CH(CH$_3$)—CH$_2$— | $\overset{O}{\underset{CNH_2}{\|}}$ | NH | —CH$_2$CH$_2$C$_6$H$_5$ |
| 26. | (CH$_2$)$_2$ | —CH$_2$—C(CH$_3$)$_2$— | $\overset{O}{\underset{CNOH,H}{\|}}$ | O | —CH$_2$—CH$_2$NHCH$_3$ |

-continued

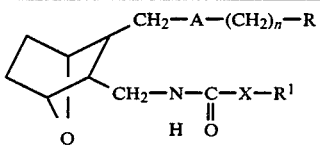

| Ex. No. | A | (CH$_2$)$_n$ | R | X | R$^1$ |
|---|---|---|---|---|---|
| 27. | CH=CH | CH$_2$ | $\underset{CN(CH_3)_2}{\overset{O}{\parallel}}$ | NH | —CH$_2$—NHCH$_3$ |
| 28. | (CH$_2$)$_2$ | (CH$_2$)$_2$ | $\underset{\underset{OH}{\mid}}{\underset{CN-CH_3}{\overset{O}{\parallel}}}$ | CH$_2$ | —NHC$_6$H$_5$ |
| 29. | CH=CH | (CH$_2$)$_3$ | CO$_2$H | O | —NCH$_3$(C$_2$H$_5$) |
| 30. | (CH$_2$)$_2$ | (CH$_2$)$_4$ | CH$_2$OH | — | —N(CH$_3$)$_2$ |
| 31. | CH=CH | —CH$_2$C(F)(F)— | tetrazole | —CH=CH— | —CH$_3$S |
| 32. | (CH$_2$)$_2$ | —CH$_2$—C(CH$_3$)(CH$_3$)— | $\underset{CN(C_2H_5)_2}{\overset{O}{\parallel}}$ | NH | —C$_4$H$_9$ |
| 33. | CH=CH | (CH$_2$)$_5$ | $\underset{CNHC_6H_5}{\overset{O}{\parallel}}$ | O | —(CH$_2$)$_2$CH=CHCH$_3$ |
| 34. | (CH$_2$)$_2$ | —CH(CH$_3$)—CH(F)— | CH$_2$OH | O | —CH$_2$—CH$_2$OC$_6$H$_5$ |
| 35. | (CH$_2$)$_2$ | (CH$_2$)$_2$ | tetrazole | NH | —CH$_2$C$_6$H$_5$ |
| 36. | CH=CH | (CH$_2$)$_3$ | CO$_2$CH$_3$ | CH$_2$ | —OC$_4$H$_9$ |
| 37. | (CH$_2$)$_2$ | (CH$_2$)$_4$ | CO$_2$CH$_3$ | CH$_2$ | —SC$_6$H$_5$ |
| 38. | CH=CH | (CH$_2$)$_5$ | CO$_2$H | O | —CH$_2$—SC$_6$H$_5$ |

What is claimed is:

1. The cis-exo isomer of the compound having the structure

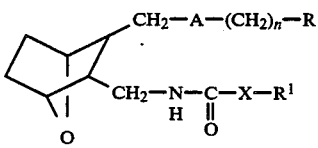

wherein A is —CH=CH— or —CH$_2$—CH$_2$—; n is 1 to 5; R is CO$_2$H, CO$_2$ alkyl, CO$_2$ alkali metal, CO$_2$ polyhydroxyamine salt, —CH$_2$OH,

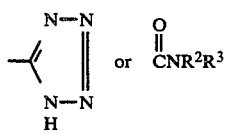

wherein R$^2$ and R$^3$ are the same or different and are H, lower alkyl, hydroxy, lower alkoxy or aryl at least one of R$^2$ and R$^3$ being other than hydroxy and lower alkoxy; X is O, NH, CH=CH OR (CH$_2$)$_x$ wherein x is 0 or 1; and R$^1$ is lower alkyl, lower alkenyl containing 2 to 12 carbons, lower alkynyl containing 2 to 12 carbons, aryl, aryl-alkyl, lower alkoxy, aryloxy, amino, alkylamino, arylamino, arylthio or alkylthio, wherein lower alkyl or alkyl alone or as part of another group contains 1 to 12 carbons and is unsubstituted or is substituted with a halo-substituent, CF$_3$, an alkoxy substituent, an aryl substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent, or an alkylthio substituent;

aryl along or as part of another group contains 6 to 10 carbons in the ring portion and is unsubstituted or is substituted with 1 to 2 lower alkyl groups, 1 or 2 halogens, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and or 1 or 2 alkylthio groups, and;

cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxyl groups, 1 or 2 aklylamino groups, 1 or 2 alkanoylamino groups, 1 or 2 arylcarbonylamino groups, 1 or 2 amino groups, 1 or 2 nitro groups, 1 or 2 cyano groups, 1 or 2 thio groups and/or 1 or 2 alkylthio groups.

2. The compound as defined in claim 1 wherein x is O.

3. The compound as defined in claim 1 wherein X is NH.

4. The compound as defined in claim 1 wherein X is $(CH_2)_x$ wherein x is 1.

5. The compound as defined in claim 1 wherein A is CH=CH.

6. The compound as defined in claim 1 wherein n is 2 to 4.

7. The compound as defined in claim 1 wherein R is $CO_2$ alkyl or $CO_2H$.

8. The compound as defined in claim 1 wherein $R^1$ is aralkyl.

9. The compound as defined in claim 1 wherein A is —CH=CH—, n is 2 to 4, R is $CO_2$ alkyl or $CO_2H$, X is O, $CH_2$ or NH and $R^1$ is benzyl.

10. The compound as defined in claim 1 having the name [1β,2α(5Z),3α,4β]-7-[3-[[[(phenylmethoxy)carbonyl]amino]methyl]-7-oxabicyclo[2.2.1]hept-2-yl]-5-heptenoic acid or esters thereof.

11. The compound as defined in claim 1 having the name [1α,2β-(5Z),3β,4α]-7-[3-[[(1-oxo-3-phenylpropyl)amino]methyl]-7-oxabicyclo[2.2.1]hept-2-yl]-5-heptenoic acid or esters thereof.

12. The compound as defined in claim 1 having the name [1β,2α(5Z),3α,4β]-7-[3-[[[(phenylmethyl)amino]carbonyl]amino]methyl]-7-oxabicyclo[2.2.1]hept-2-yl]-5-heptenoic acid or esters thereof.

13. A method of inhibiting platelet aggregation or bronchoconstriction, which comprises administering to the circulatory system of a mammalian host an effective amount of a compound as defined in claim 1 or a pharmaceutically acceptable salt thereof.

14. The method as defined in claim 13 wherein said compound is administered in an amount within the range of from about 1 to about 100 mg/kg.

15. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

16. A method of inhibiting bronchoconstriction associated with asthma, which comprises administering to a mammalian host an effective amount of a compound as defined in claim 1 or a pharmaceutically acceptable salt thereof.

17. A method of treating peripheral vascular diseases, which comprises topically or systemically administering to a mammalian host an effective amount of a compound as defined in claim 1 or a pharmaceutically acceptable salt thereof.

* * * * *